(12) United States Patent
Wu et al.

(10) Patent No.: US 11,911,154 B2
(45) Date of Patent: Feb. 27, 2024

(54) SKIN-ATTACHED BLOOD OXYGEN SATURATION DETECTION SYSTEM AND PREPARATION METHOD THEREOF

(71) Applicant: HUAZHONG UNIVERSITY OF SCIENCE AND TECHNOLOGY, Hubei (CN)

(72) Inventors: Hao Wu, Hubei (CN); Xin Huang, Hubei (CN); Ganguang Yang, Hubei (CN)

(73) Assignee: HUAZHONG UNIVERSITY OF SCIENCE AND TECHNOLOGY, Hubei (CN)

( * ) Notice: Subject to any disclaimer, the term of this patent is extended or adjusted under 35 U.S.C. 154(b) by 159 days.

(21) Appl. No.: 17/170,837

(22) Filed: Feb. 8, 2021

(65) Prior Publication Data
US 2021/0177319 A1  Jun. 17, 2021

(30) Foreign Application Priority Data
Dec. 13, 2019  (CN) .......................... 201911284119.5

(51) Int. Cl.
*A61B 5/1455* (2006.01)
*A61B 5/00* (2006.01)

(52) U.S. Cl.
CPC ........ *A61B 5/14551* (2013.01); *A61B 5/0022* (2013.01); *A61B 5/6833* (2013.01); *A61B 2562/12* (2013.01); *A61B 2562/164* (2013.01)

(58) Field of Classification Search
CPC . A61B 5/14551; A61B 5/0022; A61B 5/6833; A61B 2562/12; A61B 2562/164; A61B 5/14552
See application file for complete search history.

(56) References Cited

U.S. PATENT DOCUMENTS

| 2007/0123756 A1* | 5/2007 | Kitajima | ............ | A61B 5/14552 600/595 |
| 2013/0060109 A1* | 3/2013 | Besko | ................ | A61B 5/14552 600/323 |

(Continued)

OTHER PUBLICATIONS

Madhura Jamkhedkar, Kaustubh Jawalekar, Sayali Gawande, Wrushali Mendre, "Biometric Wrist Band", Apr. 2016, International Journal of New Technology and Research, vol. 2, Issue 4, pp. 65-68 (Year: 2016).*

(Continued)

*Primary Examiner* — Eric F Winakur
*Assistant Examiner* — Abid A Mustansir
(74) *Attorney, Agent, or Firm* — JCIPRNET

(57) ABSTRACT

The disclosure discloses a skin-attached blood oxygen saturation detection system and a preparation method thereof. The system includes a front-end flexible blood oxygen saturation detection circuit and a back-end signal processing output module connected to each other. The front-end flexible blood oxygen saturation detection circuit uses a flexible packaging material to act as a packaging layer, a surface of the front-end flexible blood oxygen saturation detection circuit has an adhesive functional layer, and is configured to detect blood oxygen saturation of a human tissue through a reflective optical principle. The back-end signal processing output module is configured to transmit a blood oxygen saturation signal to a mobile terminal through a Bluetooth antenna transmission module.

7 Claims, 3 Drawing Sheets

(56) References Cited

U.S. PATENT DOCUMENTS

| | | | | |
|---|---|---|---|---|
| 2013/0304147 | A1* | 11/2013 | Aoyama | G16H 20/30 |
| | | | | 455/66.1 |
| 2015/0230743 | A1* | 8/2015 | Silveira | A61B 5/14552 |
| | | | | 600/323 |
| 2015/0305974 | A1* | 10/2015 | Ehrenreich | A61B 5/6833 |
| | | | | 601/46 |
| 2018/0249919 | A1* | 9/2018 | Pont | A61B 5/14552 |
| 2020/0330012 | A1* | 10/2020 | Lamego | A61B 5/0004 |

OTHER PUBLICATIONS

Wonjun Lee, Youngsun Han, Chulwoo Kim, Jae-sung Rieh, Jongsun Park, Jae Young Park, and Seon Wook Kim, "Ultra-low-power Pulse Oximeter with a 32.768 kHz Real Clock", Apr. 2017, IEIE Transactions on Smart Processing and Computing, vol. 6, No. 2 (Year: 2017).*

Yue Li, Lu Zheng, Xueman Wang, "Flexible and wearable healthcare sensors for visual reality health-monitoring", Jul. 2019, Virtual Reality and Intelligent Hardware vol. 1, Issue 4, p. 411-427 (Year: 2019).*

Texas Instrument "TPS6107 Data Sheet", pp. 1-20 (Year: 2015).*

* cited by examiner

SKIN-ATTACHED BLOOD OXYGEN SATURATION DETECTION SYSTEM AND PREPARATION METHOD THEREOF

CROSS-REFERENCE TO RELATED APPLICATION

This application claims the priority benefit of China application serial no. 201911284119.5, filed on Dec. 13, 2019. The entirety of the above-mentioned patent application is hereby incorporated by reference herein and made a part of this specification.

BACKGROUND

Technical Field

The disclosure relates to the field of medical health detection devices, and in particular, relates to a skin-attached blood oxygen saturation detection system and a preparation method thereof, and the detection system is used for achieving non-invasive human blood oxygen health monitoring.

Description of Related Art

With continuous development of electronic information technology, in recent years, plastic electronics, organic electronics, printed electronics and other emerging electronics fields related to the field of flexible electronics have emerged. Since flexible electronics may be manufactured on a large scale, requires low costs, and exhibits advantages such as unique malleability and good wearability, flexible electronics are widely used in medical, energy, military, education, and other fields. Printed RFID, flexible displays, organic light-emitting diodes OLED, etc. are among the flexible electronic products that have been developed currently. Different from the conventional hard circuits, flexible electronics may provide functions such as bending, stretching, and extending, which are widely used in real life. Conventional micro-nano electronics use photolithography, electron beam, and ion beam etching processes to achieve micro-nano-scale processing. Such process is complicated, requires high manufacturing costs, and demands high environmental requirements, so it is difficult for such process to meet the large-area, batch-oriented, and highly adaptable production requirements of the flexible electronics. Therefore, in the key technologies of manufacturing of flexible electronics such as structural patterning and high-reliability packaging, development of stable and efficient process methods is an important issue.

The photoplethysmogram method is applied in most of the conventional blood sample detection principles. This principle mainly uses the difference in blood absorption of light when the human blood vessels beat to measure blood oxygen saturation. The blood oxygen sensor is mainly composed of two parts: a photoelectric converter and a light source. The light source uses light-emitting diodes with specific wavelengths that are selective for oxyhemoglobin ($HbO_2$) and deoxyhemoglobin (Hb) for detection. The reflected light is received by the photoelectric converter, and the photoelectric signal is converted and amplified. Further, based on the Beer-Lambert law as the theoretical basis, the blood oxygen saturation at the corresponding time is calculated in real time.

At present, rigid circuit boards are used by most of the commercial blood oxygen detection and sensing systems on the market, and fingertips are required to be clamped for measurement. In this method, only a single part is measured. Further, changes in human body movements may greatly reduce the adhesion of the sensing system, and detection accuracy and comfort are significantly affected as a result. At present, no blood oxygen saturation measurement system that may be closely adhered to the skin is provided on the market. In addition to the limitation of the measurement positions and difficulty of achieving measurement accuracy, the integration of the front-end test circuits and the back-end signal analysis and processing circuits of most of the blood oxygen sensing systems is low, and the volume of the circuits is large, so low portability is provided. Moreover, when the front-end circuit performs human blood oxygen detection, the back-end circuit often needs to be connected to a computer, a monitor, and other apparatuses to display and feed back the blood oxygen saturation and cannot communicate with commonly used mobile terminals, so poor mobility and wearability are provided.

SUMMARY

According to the above technical defects or improvement requirements of the related art, the disclosure provides a skin-attached blood oxygen saturation detection system and a preparation method thereof. In the disclosure, a structure and arrangement of each component in the system, connection relationships and cooperative operation among the components, and the overall process design of corresponding preparation method and the like are improved. A front-end flexible blood oxygen saturation detection circuit and a back-end signal processing output module are provided, and the front-end blood oxygen saturation detection circuit may be closely attached to and conforms to the human skin through the designed structure and the use of a flexible material. Through circuit design, the back-end signal processing output module may receive, process, and transmit front-end sensing data. A mobile terminal is used to receive and further display blood oxygen sensing data, and in this way, blood oxygen saturation information is transmitted and displayed in real-time. Moreover, the screen printing process may be directly adopted by the preparation method provided by the disclosure. Compared with the conventional micro-nano preparation processes such as photolithography, electron beam, and ion beam etching, this process is simple, requires low manufacturing costs, and is conducive to large-area and batch industrial production.

To realize the above purpose, according to one aspect of the disclosure, a skin-attached blood oxygen saturation detection system is provided and includes a front-end flexible blood oxygen saturation detection circuit and a back-end signal processing output module.

The front-end flexible blood oxygen saturation detection circuit uses a flexible packaging material to act as a packaging layer, and a surface of the front-end flexible blood oxygen saturation detection circuit has an adhesive functional layer. The adhesive functional layer is configured to be directly adhered to skin of a user so that the skin-attached blood oxygen saturation detection system is entirely adhered to the skin of the user. The front-end flexible blood oxygen saturation detection circuit is configured to noninvasively detect blood oxygen saturation of a human tissue through a reflective optical principle to obtain a blood oxygen saturation signal.

The back-end signal processing output module is connected to the front-end flexible blood oxygen saturation detection circuit. The back-end signal processing output module processes a signal detected and obtained by the front-end flexible blood oxygen saturation detection circuit. Ambient light interference is reduced first through filtering. A ratio of projection light intensity in a same pulsation process is found through searching a peak-to-valley value. A blood oxygen saturation value is calculated through a formula of $$SpO_2 = A + B * \frac{D_1}{D_2},$$

and in the formula, both A and B are predetermined constants, $D_1$ represents a ratio of an absorption peak-to-valley value of light intensity with a wavelength $\lambda_1$, D2 represents a ratio of an absorption peak-to-valley value of light intensity with a wavelength $\lambda_2$, and $\lambda_1$ and $\lambda_2$ are both predetermined. Another calculation formula is $SpO_2=a*(D_1/D_2)^2+b*(D_1/D_2)+c$, a, b and c are predetermined constants. $D_1$ and $D_2$ are the same as above. The calculated blood oxygen saturation value is sent to a mobile terminal through a Bluetooth antenna transmission module. The mobile terminal finally obtains a calculation result of the blood oxygen saturation of the user based on the blood oxygen saturation signal.

In a preferred embodiment of the disclosure, the front-end flexible blood oxygen saturation detection circuit includes a flexible substrate layer, a wire layer, a chip layer, a flexible packaging layer, and the adhesive functional layer. The flexible substrate layer and the flexible packaging layer are configured to construct and form a flexible frame body of the front-end flexible blood oxygen saturation detection circuit. The wire layer and the chip layer are both located in the flexible frame body. The chip layer is configured to noninvasively detect the blood oxygen saturation of the human tissue through the reflective optical principle. The wire layer is configured to transmit an electrical signal of the chip layer.

In a preferred embodiment of the disclosure, the front-end flexible blood oxygen saturation detection circuit specifically uses a MAX30102 chip to detect the blood oxygen saturation of the human tissue through the reflective optical principle. Conductive silver paste exhibiting a stretchable property after curing is further used as a wire to transmit the electrical signal in the front-end flexible blood oxygen saturation detection circuit. The conductive silver paste is prepared by mixing and stirring silver powder and polydimethylsiloxane according to a mass ratio of 3:1.

The flexible packaging material is polydimethylsiloxane (PDMS).

The adhesive functional layer is polypropylene, polyvinyl alcohol, silica gel Silbione RT4717 or MG7-9850.

In a preferred embodiment of the disclosure, the back-end signal processing output module includes a CC2640 core processor module, a 32.768 KHz and 4 MHz clock circuit, a reset circuit, a program downloading module, and an I²C communication port.

The CC2640 core processor module mainly includes X32KQ1, X32KQ2, X24MP, X24MN, TMSC, TCKC, TDI, TDO, RESET, RFN, RFP, SCL, SDA, and INT ports. The X32KQ1, X32KQ2, X24MP, and X24MN ports of the CC2640 core processor module are connected to an input end of the 32.768 KHz and 4 MHz clock circuit. The TMSC, TCKC, TDI, and TDO ports of the CC2640 core processor module are connected to a signal input end of the program downloading module to implement program recording. The RESET port of the CC2640 core processor module is connected to a signal input end of the reset circuit. The SCL, SDA, and INT ports of the CC2640 core processor module are connected to a signal input end of the I²C communication port. The RFN and RFP ports of the CC2640 core processor module are connected to a signal input end of the Bluetooth antenna transmission module.

In a preferred embodiment of the disclosure, the back-end signal processing output module further includes a power supply module, and the power supply module includes a CR2032 button battery power supply module and a battery boost power supply module. The CR2032 button battery power supply module is configured to provide a fixed voltage, and the battery boost power supply module is configured to raise the fixed voltage provided by the CR2032 button battery power supply module to a required voltage for circuit operation.

The battery boost power supply module is a TPS61070DDCR3.3V boost module. An input end of the TPS61070DDCR3.3V boost module is connected to an output end of the CR2032 button battery power supply module, and the TPS61070DDCR3.3V boost module is configured to raise the fixed voltage provided by the CR2032 button battery power supply module to 3.3V. A 3.3V voltage output end of the TPS61070DDCR3.3V boost module is connected to a voltage input VCC port of the CC2640 core processor module. A 1.8V voltage output end of the TPS61070DDCR3.3V boost module is connected to a voltage input port of the front-end flexible blood oxygen saturation detection circuit.

The back-end signal processing output module further includes a 3.3V decoupling module. The 3.3V decoupling module is configured to be connected to an output end of the TPS61070DDCR3.3V boost module such that coupling noise of a 3.3V output voltage is reduced. The 3.3V decoupling module is preferably formed by three 100 nF chip capacitors connected in parallel.

In a preferred embodiment of the disclosure, the back-end signal processing output module is connected to the front-end flexible blood oxygen saturation detection circuit through an FPC connection flexible flat cable. The front-end flexible blood oxygen saturation detection circuit transmits the detected and obtained blood oxygen saturation signal to the back-end signal processing output module through the FPC connection flexible flat cable. The back-end signal processing output module supplies power and also provides a ground potential to the front-end flexible blood oxygen saturation detection circuit through the FPC connection flexible flat cable.

In a preferred embodiment of the disclosure, a volume of the front-end flexible blood oxygen saturation detection circuit is less than 18 mm×18 mm×2 mm. The back-end signal processing output module is a single-layer circuit, and an area of the back-end signal processing output module is less than 28 mm×28 mm.

In a preferred embodiment of the disclosure, the mobile terminal is a mobile phone.

According to another aspect of the disclosure, a preparation method for preparing the foregoing skin-attached blood oxygen saturation detection system is provided and includes the following steps.

(1) The front-end flexible blood oxygen saturation detection circuit is to be prepared.

The polydimethylsiloxane (PDMS) is cured on a hard substrate by spin coating first to obtain the flexible substrate layer mainly composed of polydimethylsiloxane. A conductive silver paste layer satisfying a pre-designed circuit pattern on the flexible substrate layer is prepared by blade coating to form the wire layer. The prepared flexible substrate layer and the conductive silver paste layer thereon are allowed to be peeled off from the hard substrate as a whole and transferred to another hard substrate that is not adhered to PDMS. A plurality of chips are connected to pre-set target positions of the conductive silver paste layer to obtain a chip layer, and the conductive silver paste layer is cured so that the wire layer is formed after curing.

The chip layer includes a 1.8V step-down chip, a first pull-up resistor, a second pull-up resistor, a third pull-up resistor, a decoupling capacitor, and a MAX30102 chip. Pins of each chip are adhered to the conductive silver paste layer by lightly touching and pressing after being coated with the conductive silver paste. The pins of the chip layer are fixedly connected after curing in a 150° C. to 170° C. oven for 1 to 1.5 hours and then naturally cooling to 80° C. to 100° C.

Polydimethylsiloxane is poured next on the chip layer to act as the flexible packaging layer, and each chip is cured and protected after being cured in a 40° C. to 80° C. oven for 2 to 4 hours.

An organic polymer layer is prepared on the flexible packaging layer to act as the adhesive functional layer so that the front-end flexible blood oxygen saturation detection circuit is prepared and obtained.

(2) The FPC connection flexible flat cable and the back-end signal processing output module are to be connected.

Same ends of 5 connection ports VIN, SCL, SDA, INT, and GND of the FPC connection flexible flat cable are adhered to the wire layer of the front-end flexible blood oxygen saturation detection circuit through the conductive silver paste. Other ends with 2.54 mm single row five-hole pins are fixedly connected by soldering so that the front-end flexible blood oxygen saturation detection circuit and the FPC connection flexible flat cable are connected. The 2.54 mm single row five-hole pins are subsequently configured for soldering on VIN, SCL, SDA, INT, and GND jacks of the back-end signal processing output module. Different pins of the back-end signal processing output module are connected to the VIN, SCL, SDA, INT, and GND jacks, so that the back-end signal processing output module is connected to the front-end flexible blood oxygen saturation detection circuit through the FPC connection flexible flat cable. The skin-attached blood oxygen saturation detection system is finally obtained.

In a preferred embodiment of the disclosure, step (1) of preparing the conductive silver paste layer satisfying the pre-designed circuit pattern on the flexible substrate layer by blade coating further includes the following steps. The conductive silver paste is blade coated with a flat blade. The conductive silver paste penetrates a polyester screen printed with the circuit pattern as being extruded by the blade, so that the conductive silver paste layer with the pre-designed circuit pattern is formed on the flexible substrate layer.

The above technical solutions provided by the disclosure have the following beneficial effects compared with the related art.

(1) The skin-attached blood oxygen saturation detection system provided by the disclosure is also a wearable flexible blood oxygen saturation detection system. The skin-attached blood oxygen saturation detection system is wearable, may be used to detect blood oxygen saturation of a human body in real time, may transmit blood oxygen data to a mobile terminal through Bluetooth, and may feed back the blood oxygen data in real time. The front-end flexible blood oxygen saturation detection circuit noninvasively detects blood oxygen saturation of a human tissue through the reflective optical principle to obtain a blood oxygen saturation signal. The back-end signal processing output module may receive data from a sensor and transmits the data to a mobile terminal such as a mobile phone through Bluetooth. Preferably, the volume of the front-end flexible blood oxygen saturation detection circuit does not exceed 18 mm×18 mm×2 mm. The back-end signal processing output module is a single-layer circuit, and preferably, the area thereof does not exceed 28 mm×28 mm, so the entire system is compact and light-weighted with good stability and high measurement accuracy.

(2) Regarding the front-end flexible blood oxygen saturation detection circuit provided by the disclosure, PDMS is adopted by the front-end flexible blood oxygen saturation detection circuit as the substrate, and self-made conductive paste is adopted as the wire layer. The circuit exhibits good stretchability, malleability, and a small volume. An adhesive layer (i.e., the adhesive functional layer) is added to the PDMS packaging layer. Polypropylene, polyvinyl alcohol, silicone Silbione RT 4717 and MG7-9850 act as an example to prepare the adhesive layer. The peeling energy of the adhesive layer is 10 times that of an ordinary PDMS material (i.e., Sylgard184), so that the prepared system may be well attached to the part of the body to be tested and has strong anti-interference. These adhesive functional materials, on the one hand, are flexible, and on the other hand, exhibit good biocompatibility and do not react with PDMS.

Regarding the front-end flexible blood oxygen saturation detection circuit provided by the disclosure, the flexible polymer material polydimethylsiloxane is used as the packaging layer, and the adhesive polymer material is used as the adhesive functional layer, and the electronic components used are encapsulated and packaged by the flexible material. Using flexible materials as the packaging material of the circuit gives the entire circuit the ability to withstand a certain degree of deformation, so that the circuit may be deformed together with the human skin. The adhesive polymer material gives the ability to be adhered closely to the skin. Through preparation of a thin organic polymer layer with good adhesion to act as the adhesive functional layer, a device may be adhered and fixed onto the skin to allow the device to be in contact with the skin for a long time.

(3) Further, in the preparation process, the flexible substrate is peeled off in advance after the screen printing of the wire layer, and in this way, the peeling operation after the system is prepared is prevented from damaging the hard electronic components in the system and affecting the normal operation of the system.

(4) The back-end signal processing output module adopted by the disclosure is designed according to features of the front-end flexible blood oxygen saturation detection circuit. The use of low-power Bluetooth communication as the communication method between the system and the mobile terminal enhances wearability of the system. The CC2640 core processor module is preferably adopted by the back-end signal processing output module. The CC2640 core processor module chip comes with a 2.4 GHz antenna to achieve wireless communication while ensuring ultra-low power consumption. Further, power is supplied by the 3VCR2032 button battery, as such, long-term real-time blood oxygen detection is achieved and long battery life is provided.

To sum up, since screen printing is adopted by the disclosure, large-area and batch preparation of flexible circuits may be achieved. In the disclosure, conductive silver paste with a specific composition ratio and may be stretched after curing is particularly used. The silver powder and polydimethylsiloxane are mixed and stirred according to a mass ratio of 3:1 to prepare the conductive silver paste with the specific composition ratio and may be stretched after curing, and in this way, the yield of the device is further ensured. In the skin-attached blood oxygen saturation detection system provided by the disclosure, first, regarding the circuit substrate in the design and preparation of the front-end flexible blood oxygen saturation detection circuit, in some processes or commercial devices used by other scholars, hard substrates or bendable but non-stretchable substrates (such as polyimide (PI), polyethylene terephthalate (PET), etc.) are used most of the time at present. None of the detection circuits prepared based on the above-mentioned substrate materials may maintain conformal contact with the skin and provides poor wearability, so the signal is easily interfered during the measurement process. In the disclosure, the flexible and stretchable PDMS is adopted to act as the substrate, conformal attachment between the front-end measurement circuit and the skin is ensured, and wearability of the system and accuracy of the measurement signal are improved. In the preparation of flexible circuit wires, other scholars usually use conventional micro-nano processing techniques such as photolithography to prepare patterned wires. Benefiting from the fluidity of the flexible conductive material used before curing, the high conductivity and high stretchability after curing, and good adhesion to the flexible substrate, in the disclosure, the preparation of the flexible circuit patterned wire is achieved by using flexible conductive materials and the screen printing process. That is, in the disclosure, the front-end circuit is composed of a combination of soft and hard materials, the substrate and the wires are flexible and stretchable, the electronic components are hard, and the overall system may be stretched and curled and may keep working normally in a stretched and curled state. Next, in terms of attaching the sensor to the skin, in the pre-development process, in order to make the sensor be closely adhered to the skin, external fixation such as bandages, wristbands, etc. are needed to greatly limit the area where it can be attached. In order to break through the limitation, in the disclosure, adhesive functional materials (such as polypropylene, polyvinyl alcohol, silica gel Silbione RT4717, MG7-9850 etc.) are used to achieve close adhesion to the skin. In addition, in terms of signal processing and transmitting system integration, during the research and development process, for the design of the back-end signal processing and transmission system, some of the existing design schemes may make the back-end system larger and be provided with complicated wiring. In the disclosure, by selecting chips with control and Bluetooth transmission functions, the overall volume of the system is reduced and the wiring between different modules is simplified.

Through the overall design of a specific preparation process, the yield is significantly improved in the disclosure. Generally, the manufacturing process of the flexible circuit in the prior art is to peel off the whole circuit after the preparation is completed. Nevertheless, in the disclosure, since peeling off of the entire circuit may cause the electronic components to be separated from the substrate, in the preparation process, the disclosure chooses to directly peel off and transfer the printed wire to a substrate that is not adhered to PDMS and then proceeds to the subsequent circuit preparation process. In this way, the influence of the peeling off process on the circuit is avoided. Further, in the disclosure, the mesh number of the screen used in the screen printing is controlled to 300 meshes, and the height between the bottom surface of the screen and the target deposition surface is controlled to 2 mm. Such configuration may be applied to prepare wires with good conductivity and having spacing between wires to be 0.4 mm, and the problems of thin printed wires and poor conductivity caused a screen having a small mesh number are thereby avoided. The easy connection problem among adjacent printed wires and the subsequent short circuit problem caused by a screen with a large mesh number are avoided. The problem of thin printed wires easily caused by excessively high height, the problem of poor conductivity, and the short circuit problem which occurs among adjacent wires caused by excessively low height are also avoided.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

To better illustrate the goal, technical solutions, and advantages of the disclosure, the following embodiments accompanied with drawings are provided so that the disclosure are further described in detail. It should be understood that the specific embodiments described herein serve to explain the disclosure merely and are not used to limit the disclosure. In addition, the technical features involved in the various embodiments of the disclosure described below can be combined with each other as long as the technical features do not conflict with each other.

The disclosure provides a wearable flexible blood oxygen saturation detection system. The wearable flexible blood oxygen saturation detection system may be used to detect blood oxygen saturation in real time and transmits blood oxygen data to a remote mobile terminal via a Bluetooth antenna to feed back the blood oxygen data.

Figure 1:
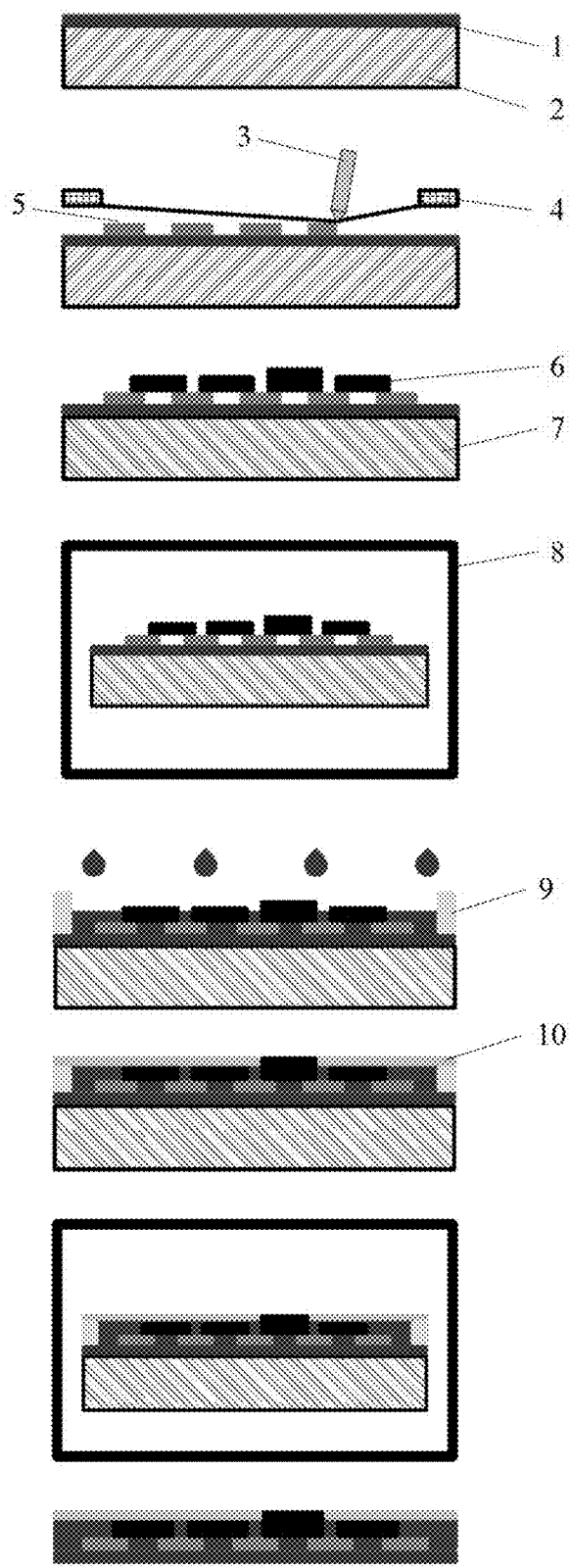
FIG. 1 is a schematic view of a manufacturing process of a front-end flexible blood oxygen saturation detection circuit of a wearable flexible blood oxygen saturation detection system.

FIG. 1 is a schematic view of a manufacturing process of a front-end flexible blood oxygen saturation detection circuit of a wearable flexible blood oxygen saturation detection system. A preparation process of the front-end flexible blood oxygen saturation detection circuit is described in combination with the embodiments.

Embodiment 1

Sylgard 184 polydimethylsiloxane (PDMS) may be used, and a mass ratio of prepolymer to a curing agent may be 11:1. The prepolymer and the curing agent are evenly mixed for 5 to 8 minutes to obtain PDMS. The PDMS is placed in a vacuum box to be vacuumed and is left to stand for 40-60 minutes. After the bubbles in the PDMS are all eliminated, the PDMS may be removed after standing. The pressure of the vacuum box is 0 to 0.1 atmospheres.

Next, the PDMS is evenly coated on an ordinary hard substrate 2 after standing. For instance, the ordinary hard substrate 2 coated with the PDMS may be placed on a platform of a spin coater. The spin coater may be set to a single-step spin coating mode, that is, a rotation speed of 600 rpm/min, acceleration of 500 rpm$^2$/min, and spin coating time of 30 seconds are selected, and in this way, the PDMS with a uniform thickness is provided on the ordinary hard substrate 2. After the spin coating is completed, the ordinary hard substrate 2 spin-coated with the PDMS is allowed to stand at room temperature for 1 to 2 minutes and then is placed on a hot plate. The temperature is adjusted to 60 degrees, and the curing time is 40 minutes, and a flexible substrate layer 1 is produced on the ordinary hard substrate 2.

Next, a polyester screen 4 printed with a circuit pattern is fixed on a screen printer, and a model adopted by the polyester screen 4 may be a 300-mesh screen. The polyester screen 4 on the screen printer is adjusted to a horizontal center position, and after a height of 2 mm from a platform of the screen printer is provided, the hard substrate 2 coated with the flexible substrate layer 1 is placed on the platform of the screen printer. A plane position of the platform of the screen printer is adjusted. The circuit pattern of the polyester screen 4 is ensured to be located in the center of the hard substrate (the circuit pattern of the polyester screen 4 is pre-designed so that a wire distribution of a wire layer obtained according to the circuit pattern satisfies a predetermined requirement, since an overall size of the polyester screen 4 is required to match a size of a jig of the platform of the screen printer, and an actual size of the circuit pattern is small, the circuit pattern occupies only a small area in the center of the polyester screen 4, and an overall size of the hard substrate is also smaller than the size of the polyester screen 4, so the position of the platform is required to be adjusted so that the circuit pattern corresponds to the center of the substrate). After such adjustment is completed, conductive silver paste 5 is evenly spread on a portion of the polyester screen 4 with the circuit pattern. A blade 3 may be adopted. For instance, the blade 3 may be held with a single hand with an inclination angle of 45 degrees. The middle finger is put in the middle of the blade 3 to scrape across the polyester screen 4 at a constant speed, and the speed is kept to be at 2 cm/s to ensure that the conductive silver paste 5 is evenly coated on the flexible substrate layer 1 to form a conductive silver paste layer 5. The conductive silver paste 5 is prepared by mixing and stirring commercial silver powder (such as AgF-3C silver powder) and polydimethylsiloxane according to a mass ratio of 3:1.

After that, the flexible substrate layer 1 coated with the conductive silver paste layer 5 is then peeled from the hard substrate 2 as a whole and is transferred to a surface (e.g., sandpaper) of a hard substrate 7 that is not adhered to the PDMS, and the entirely independent flexible substrate layer 1 and the conductive silver paste layer 5 are obtained.

Next, a MAX30102 chip 603, a first decoupling capacitor 601, a second decoupling capacitor 602, a first pull-up resistor 604, a third decoupling capacitor 605, a second pull-up resistor 606, a third pull-up resistor 607, and a XC6206P182MR608 step-down chip are clamped with a needle nose tweezer, are aligned with corresponding chip packaging pins on the wire layer, and are gently placed. The corresponding chip packaging pins are gently pressed by a tip end of the needle nose tweezer, and a chip layer 6 and the conductive silver paste layer 5 are adhered in this way. The system having the adhered chip layer 6 is placed in an oven 8 for curing at 160 degrees for 1 hour and 20 minutes and is then cooled to 90 degrees at room temperature. In this way, the conductive silver paste layer 5 and the chip layer 6 are fixedly connected, the conductive silver paste layer 5 is cured, and favorable electrical connection is thereby provided.

Accordingly, a front-end flexible blood oxygen saturation detection circuit 17 is obtained.

Next, ports of one end of an FPC connection flexible flat cable 16 are soldered with 2.54 mm male single row pins. Each port of another end of the FPC connection flexible flat cable 16 connected to the front-end flexible blood oxygen saturation detection circuit 17 is coated with the conductive silver paste 5. The end coated with the conductive silver paste 5 is aligned with a corresponding pin port on the conductive silver paste layer 5 and is pressed gently to ensure tight adhesion. The system having the adhered FPC connection flexible flat cable 16 is placed in the oven 8 for curing at 160 degrees for 1 hour and 20 minutes and is then cooled to 90 degrees at room temperature. In this way, the FPC connection flexible flat cable 16 and the conductive silver paste layer 5 are fixedly connected, and favorable electrical connection is thereby provided.

Next, a frame mold 9 of no more than 18 mm×18 mm and a thickness of 1 mm is placed on a flexible substrate of the cured FPC connection flexible flat cable. After the frame mold 9 is fixed with a PI tape, the PDMS after standing is slowly injected into the frame mold 9. After the PDMS after standing evenly covers the entire circuit, an adhesive functional layer 10 is coated on an upper surface of the PDMS, is left to stand for 25 minutes, is placed in the oven 8 for curing at 60 degrees for 3 hours, and is taken out. A packaging layer and the adhesive functional layer 10 are manufactured above the chip layer 6. The frame mold 9 is slowly removed with a blade. A thin layer above the PDMS that is in contact with air is the adhesive functional layer 10, which exhibits good adhesion and may be closely attached to the skin to achieve wearability of the device.

Figure 2:
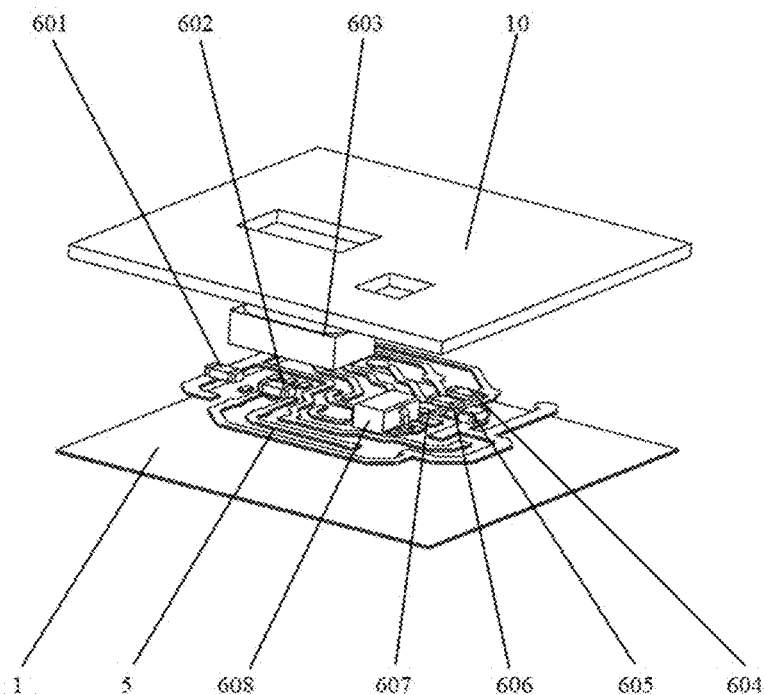
FIG. 2 is a schematic view of a three-dimensional structure of the front-end flexible blood oxygen saturation detection circuit of the wearable flexible blood oxygen saturation detection system.
Figure 3:
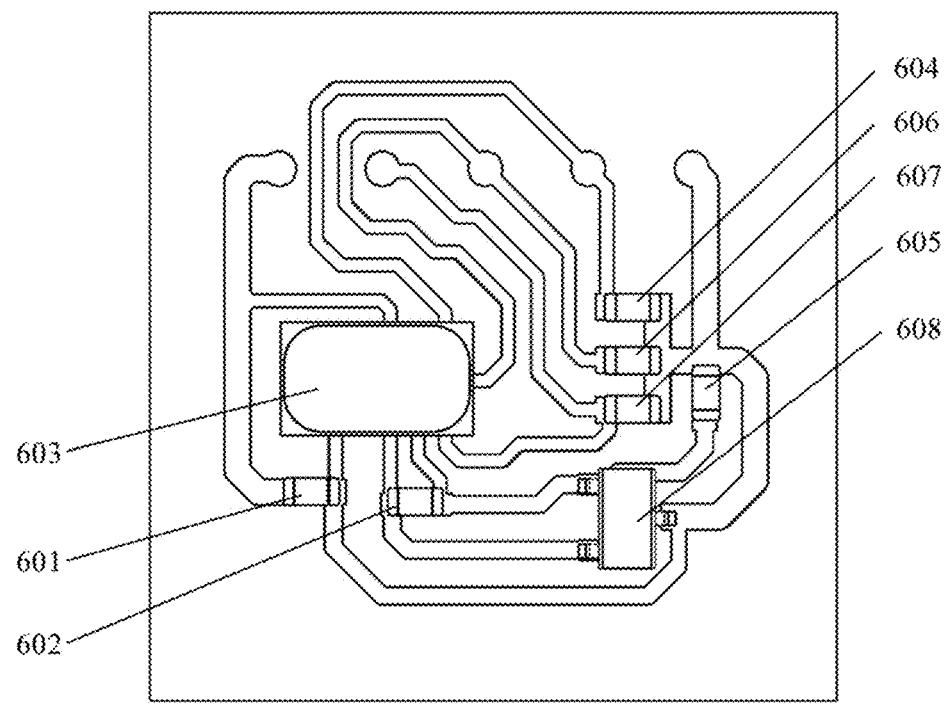
FIG. 3 is a schematic top view of a conductive silver paste layer and a chip layer.

In this embodiment, as shown in FIG. 2 and FIG. 3, the front-end flexible blood oxygen saturation detection circuit 17 includes the flexible substrate layer 1, the conductive silver paste layer 5, the chip layer, and the adhesive functional layer 10. The flexible substrate layer 1 is manufactured through spin-coating and then curing the PDMS at 90 degrees for 20 minutes. Regarding the conductive silver paste layer 5, the conductive silver paste 5 is evenly spread on the portion of the polyester screen 4 with the circuit pattern. The blade 3 is adopted to scrape across the polyester screen 4 to ensure that the conductive silver paste 5 is evenly adhered to and coated on the flexible substrate layer 1, and the conductive silver paste layer 5 is then manufactured. The chip layer mainly includes the first decoupling capacitor 601, the second decoupling capacitor 602, the MAX30102 chip 603, the first pull-up resistor 604, the third decoupling capacitor 605, the second pull-up resistor 606, the third pull-up resistor 607, and the XC6206P182MR step-down chip 608. The 1.8VXC6206P182MR step-down chip 608 may lower a 3.3V voltage to a 1.8V voltage to supply power to the MAX30102 chip 603. Output enable ends of the first pull-up resistor 604, the second pull-up resistor 606, and the third pull-up resistor 607 may be respectively connected to SCL, SDA, and INT ports of the MAX30102 chip 603 to achieve I$^2$C communication. Input ends of the pull-up resistors 604, 606, and 607 are connected to a 3.3V power line.

The decoupling capacitors 601, 602, and 605 are respectively connected in parallel with a 3.3V input end of the XC6206P182MR step-down chip 608 and a 1.8V port and a GND port of the MAX30102 chip 603 to achieve decoupling and noise reducing of the power line. The MAX30102 chip 603 adopts a radiation optical path to detect blood oxygen saturation and collect data. After being coated with the conductive silver paste 5, pins of the chip layer are adhered to the conductive silver paste layer 5 through gentle touching and pressing. The pins of the chip layer 6 may be fixedly connected after conductive paste of the conductive silver paste layer 5 is cured.

Herein, after passing through the enable ends of the pull pull-up resistors 604, 606, and 607, the SCL, SDA, and INT ports of the MAX30102 chip 603 transmit blood oxygen saturation data to an I²C communication port 15 of a back-end signal processing output module through the FPC connection flexible flat cable 16.

The adhesive functional layer 10 refers to preparation of a thin organic polymer layer with good adhesion (e.g., polypropylene, polyvinyl alcohol, silica gel Silbione RT4717, MG7-9850 etc.), which may adhere and fix a device onto the skin to allow the device to be in contact with the skin for a long time.

One end of each of five connection ports VIN, SCL, SDA, INT, and GND of the FPC connection flexible flat cable 16 is adhered to the conductive silver paste layer 5 through the conductive silver paste 5. Another end of each of the five connection ports VIN, SCL, SDA, INT, and GND of the FPC connection flexible flat cable 16 is fixedly connected to 2.54 mm single row five-hole pins through soldering. The 2.54 mm single row five-hole pins are soldered on VIN, SCL, SDA, INT, and GND jacks of a CC2640 core processor module 11.

Figure 4:
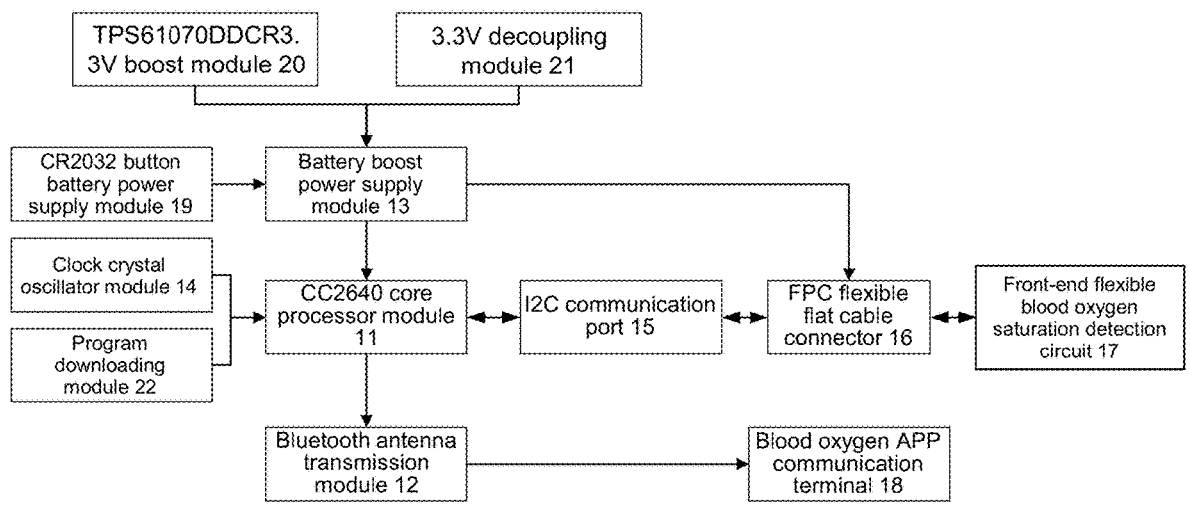
FIG. 4 is a schematic view of a circuit principle of the wearable flexible blood oxygen saturation detection system.

In this embodiment, as shown in FIG. 4, in the circuit principles adopted by the wearable flexible blood oxygen saturation detection system, a battery boost power supply module 13 mainly includes a CR2032 button battery power supply module 19, a TPS61070DDCR3.3V boost module 20, and a 3.3V decoupling module 21. The CR2032 button battery power supply module 19 includes a 3V output CR2032 button battery and a button battery base. An input end of the TPS61070DDCR boost module 20 is connected to an output end of the CR2032 button battery power supply module 19. An output end of the TPS61070DDCR boost module 20 is connected to a VCC port of the CC2640 core processor module 11 and a VIN port (i.e., a voltage input port) of the front-end flexible blood oxygen saturation detection circuit 17. The 3.3V decoupling module 21 connects 3 100 nF chip capacitors in parallel between the output end and a GND of the TPS61070DDCR boost module 20, such that coupling noise of a 3.3V output voltage is reduced.

The CC2640 core processor module 11 mainly includes a 32.768 KHz and 4 MHz clock circuit 14, a program downloading module 22, the I²C communication port 15, and a Bluetooth antenna transmission module 12. The CC2640 core processor module 11 mainly includes X32KQ1, X32KQ2, X24MP, X24MN, TMSC, TCKC, TDI, TDO, RESET, RFN, RFP, SCL, SDA, and INT ports. The X32KQ1, X32KQ2, X24MP, and X24MN ports in the CC2640 core processor module 11 are connected to an input end of the 32.768 KHz and 4 MHz clock circuit. The TMSC, TCKC, TDI, and TDO ports in the CC2640 core processor module 11 are connected to a signal input end of the program downloading module 22 to implement program recording (the program downloading module 22 may be used to download a program from a computer end into a chip, and certainly, a series of programs for data processing may be pre-written on the computer end, so the work of the chip may be achieved by recording into the chip). The SCL, SDA, and INT ports in the CC2640 core processor module 11 are connected to a signal input end of the I²C communication port 15. The RFN and RFP ports in the CC2640 core processor module 11 are connected to a signal input end of the Bluetooth antenna transmission module 12. A core controller and a processing module may share a core chip. The Bluetooth antenna transmission module 12 may include only a Bluetooth antenna and several inductive devices and capacitive devices and is mainly configured to transmit signals, load information, and control transmission rates, which may be achieved by a Bluetooth plate inside the core chip.

In the back-end signal processing output module, a processor module (e.g., the CC2640 core processor module 11) may be used to process a signal detected and obtained by the front-end flexible blood oxygen saturation detection circuit 17. Ambient light interference is reduced first through filtering. A ratio of projection light intensity in a same pulsation process is found through searching a peak-to-valley value. A blood oxygen saturation value is calculated through a formula of $$SpO_2 = A + B * \frac{D_1}{D_2}.$$

In the formula, both A and B are predetermined constants. The calculation formula can also be $SpO_2 = a*(D_1/D_2)^2 + b*(D_1/D_2)+c$. For instance, A and B may adopt the recommended configurations in the official chip application notes. Taking the MAX30102 chip 603 as an example, A=104 and B=−17 (the reference chip application notes may be found with reference to: Maxim Integrated, "Recommended Configurations and Operating Profiles for MAX30101/MAX30102 EV Kits." UG6409; Rev 0; 3/18.). For another formula, a=1.596, b=−34.659 and c=112.689 (the reference chip application notes may be found with reference to: Application Note 6845 Guidelines for $SpO_2$ Measurement Using the Maxim Max32664 Sensor Hub). And $D_1$ and $D_2$ respectively represent ratios of absorption peak-to-valley values of light intensity with wavelengths $\lambda_1$ and $\lambda_2$. $\lambda_1$ and $\lambda_2$ are determined by the chip, are predetermined as well, and are 650 nm to 670 nm and 870 nm to 900 nm respectively, for example. The calculated blood oxygen saturation value is sent to a mobile terminal through the Bluetooth antenna transmission module 12. Based on the signal of the blood oxygen saturation, functions, such as drawing of a blood oxygen saturation change curve of a user during measurement time on the mobile terminal, may be achieved.

In this way, through the CC2640 core processor module 11, signal filtering is achieved, such that ambient light interference is reduced, peak finding is performed, the peak-to-valley ratios are calculated, and peak-to-valley ratios of different light are calculated, and the blood oxygen saturation may be calculated through formula substitution. The front-end flexible blood oxygen saturation detection circuit 17 mainly receives light intensity passing through the human tissue through a photoelectric receiver. In a heartbeat interval, due to the expansion and contraction of blood vessels, the received light intensity may change. The peak-to-valley value represents the minimum and maximum blood vessel diameters. By comparing the peak-to-valley values, muscles, fat, pigment, and other factors that have constant light absorption in the heartbeat interval may be removed. The peak-to-valley ratio is only affected by the blood hemoglobin concentration and the change of blood vessel diameter. By selecting two different wavelengths of light and by comparing the peak-to-valley ratios of the two light, the influence of blood vessel diameter is eliminated, and the finally-obtained data is only related to the concentration of hemoglobin and may be put in the formula to calculate the blood oxygen saturation.

The Bluetooth antenna transmission module 12 may include a decoupling magnetic bead and a 2.4 GHz patch antenna. The decoupling magnetic bead is configured to achieve noise reduction of a wireless signal. The 2.4 GHz patch antenna is configured to transmit the blood oxygen data and simultaneously realizes wireless Bluetooth communication with a mobile terminal 18 such as a mobile phone.

In the embodiment, the CR2032 button battery power supply module 19 acts as a power supply source and supplies a 3V voltage to the entire circuit. The TPS61070DDCR3.3V boost module 20 boosts the 3V voltage supplied by the CR2032 button battery power supply module 19 to a 3.3V voltage and supplies power to the CC2640 core processor module 11. The TPS61070DDCR3.3V boost module 20 is connected to the front-end flexible blood oxygen saturation detection circuit 17 to supply the 3.3V voltage through the VIN port of the FPC connection flexible flat cable 16. The front-end flexible blood oxygen saturation detection circuit 17 is grounded through the GND port of the FPC connection flexible flat cable 16, and the entire circuit is in a working state. One side of the adhesive functional layer 10 of the front-end flexible blood oxygen saturation detection circuit 17 may be attached to the fingertip (certainly, it may also be other skin epidermal positions). The position of the MAX30102 chip 603 in the front-end flexible blood oxygen saturation detection circuit 17 is adjusted to set the MAX30102 chip 603 to be attached to the center of the finger. A surface of the MAX30102 chip is exposed and is not covered by the adhesive functional layer 10, so that a top portion of the MAX30102 chip directly contacts the skin. The MAX30102 chip 603 transmits a blood oxygen saturation data signal into the CC2640 core processor module 11 through the I²C communication port via the SCL, SDA, and INT ports in the FPC connection flexible flat cable 16. After processing the related blood oxygen saturation data signal, the CC2640 core processor module 11 may feed back human blood oxygen saturation in real time through wireless transmission to the mobile terminal 18 via the Bluetooth antenna transmission module 12 (the mobile terminal 18 is also provided with a separate "blood oxygen saturation detection APP" to show the user the obtained human blood oxygen saturation through GUI design and the like, and the blood oxygen saturation detection APP may, for example, calculate data transmitted to the mobile phone terminal, obtain real-time data of the blood oxygen saturation of human tissues, and display a graph of changes over time).

The skin-attached blood oxygen saturation detection system in the disclosure may be used together with the blood oxygen saturation detection APP in the mobile terminal. Wireless Bluetooth communication may be achieved and the blood oxygen data may be transmitted through a 2.4 GHz antenna module and the blood oxygen saturation detection APP. The mobile phone terminal may receive the blood oxygen data through development of the supporting blood oxygen saturation detection APP. The operation steps of the APP are easy, the required professional knowledge level is low, and the human-machine interaction interface is designed to be user-friendly, so the APP may be suitable to people of different ages. The following is an extended introduction to the blood oxygen saturation detection APP. The interface of this blood oxygen saturation detection APP may include four options: "search", "start", "settings", and "turn on notification". For instance, the "search" option allows the mobile terminal to detect the Bluetooth device to be connected. After the APP is connected to the Bluetooth device, the "turn on notification" option allows the reception of Bluetooth transmission data. The "start" option allows the drawing of received data. The "settings" option may be used to set the data transmission rate and the time interval between adjacent data points in the drawing.

In the foregoing embodiments, detection of attachment on finger skin is provided as an example only. According to actual needs, in addition to being attached to the skin of the fingers, the device may also be attached to relatively flat parts of the human skin such as arm skin, facial skin, or earlobe.

In the disclosure, the technical means of pre-separating and using of sandpaper as the separated substrate layer are adopted, and in this way, the separation step from the hard substrate after the system is prepared is prevented from affecting the performance of the electronic components of the system. The various components (including various functional modules, chips, etc., as shown in FIG. 4) used in the disclosure may be commercially purchased. Regarding the connection of the pins of the functional modules, chips, etc., detailed description may be found with reference to the relevant instruction manual for settings.

A person having ordinary skill in the art should be able to easily understand that the above description is only preferred embodiments of the disclosure and is not intended to limit the disclosure. Any modifications, equivalent replacements, and modifications made without departing from the spirit and principles of the disclosure should fall within the protection scope of the disclosure.

What is claimed is:

1. A blood oxygen saturation detection system, comprising:
   a front-end flexible blood oxygen saturation detection circuit,
   the front-end flexible blood oxygen saturation detection circuit comprising a flexible packaging material to act as a flexible packaging layer, and
   an adhesive functional layer positioned on a surface of the front-end flexible blood oxygen saturation detection circuit, wherein the adhesive functional layer is configured to be directly adhered to skin of a user, so that the blood oxygen saturation detection system is entirely adhered to the skin of the user, and wherein the front-end flexible blood oxygen saturation detection circuit is configured to noninvasively detect blood oxygen saturation of a human tissue through a reflective optical principle, so as to obtain a blood oxygen saturation signal,
   a CC2640 core processor, wherein the CC2640 core processor is connected to the front-end flexible blood oxygen saturation detection circuit, the CC2640 core processor is configured to process the blood oxygen saturation signal detected and obtained by the front-end flexible blood oxygen saturation detection circuit by:
   reducing ambient light interference through signal filtering, calculating a ratio of projected light intensity in a same pulsation process using a peak-to-valley value, calculating a blood oxygen saturation value through a formula of $$SpO_2 = A + B * \frac{D_1}{D_2}$$

both wherein A and B are predetermined constants, or through $SpO_2 = a*(D_1/D_2)^2 + b*(D_1/D_2) + c$, wherein a, b and c are predetermined constants, $D_1$ represents a ratio of an absorption peak-to-valley value of light intensity with a wavelength $\lambda_1$, $D_2$ represents a ratio of an absorption peak-to-valley value of light intensity with a wavelength $\lambda_2$, and $\lambda_1$ and $\lambda_2$ are both predetermined in the formula, transmitting the calculated blood oxygen saturation value to a mobile terminal through a Bluetooth antenna transmission module.

2. The blood oxygen saturation detection system according to claim 1, wherein the front-end flexible blood oxygen saturation detection circuit comprises a flexible substrate layer, a wire layer, a chip layer, the flexible packaging layer, and the adhesive functional layer, wherein the flexible substrate layer and the flexible packaging layer are configured to construct and form a flexible frame body of the front-end flexible blood oxygen saturation detection circuit, the wire layer and the chip layer are both located in the flexible frame body, the chip layer is configured to noninvasively detect the blood oxygen saturation of the human tissue through the reflective optical principle, and the wire layer is configured to transmit an electrical signal of the chip layer.

3. The blood oxygen saturation detection system according to claim 1, wherein the CC2640 core processor comprises a CC2640 core processor module, a 32.768 KHz and 4 MHz clock circuit, a reset circuit, a program downloading module, and an I²C communication port, wherein the CC2640 core processor module comprises X32KQ1, X32KQ2, X24MP, X24MN, TMSC, TCKC, TDI, TDO, RESET, RFN, RFP, SCL, SDA, and INT ports, the X32KQ1, X32KQ2, X24MP, and X24MN ports of the CC2640 core processor module are connected to an input end of the 32.768 KHz and 4 MHz clock circuit, the TMSC, TCKC, TDI, and TDO ports of the CC2640 core processor module are connected to a signal input end of the program downloading module to implement program recording, the RESET port of the CC2640 core processor module is connected to a signal input end of the reset circuit, the SCL, SDA, and INT ports of the CC2640 core processor module are connected to a signal input end of the I²C communication port, and the RFN and RFP ports of the CC2640 core processor module are connected to a signal input end of the Bluetooth antenna transmission module.

4. The blood oxygen saturation detection system according to claim 3, wherein the CC2640 core processor further comprises a power supply module, and the power supply module comprises a CR2032 button battery power supply module and a battery boost power supply module, wherein the CR2032 button battery power supply module is configured to provide a fixed voltage, and the battery boost power supply module is configured to raise the fixed voltage provided by the CR2032 button battery power supply module to a required voltage for circuit operation, the battery boost power supply module is a TPS61070DDCR3.3V boost module, an input end of the TPS61070DDCR3.3V boost module is connected to an output end of the CR2032 button battery power supply module, the TPS61070DDCR3.3V boost module is configured to raise the fixed voltage provided by the CR2032 button battery power supply module to 3.3V, a 3.3V voltage output end of the TPS61070DDCR3.3V boost module is connected to a voltage input VCC port of the CC2640 core processor module, and a 1.8V voltage output end of the TPS61070DDCR3.3V boost module is connected to a voltage input port of the front-end flexible blood oxygen saturation detection circuit, the CC2640 core processor further comprises a 3.3V decoupling module, the 3.3V decoupling module is configured to be connected to an output end of the TPS61070DDCR3.3V boost module such that coupling noise of a 3.3V output voltage is reduced, and the 3.3V decoupling module is formed by three 100 nF chip capacitors connected in parallel.

5. The blood oxygen saturation detection system according to claim 1, wherein the CC2640 core processor is connected to the front-end flexible blood oxygen saturation detection circuit through a FPC connection flexible flat cable, the front-end flexible blood oxygen saturation detection circuit transmits the blood oxygen saturation signal to the CC2640 core processor through the FPC connection flexible flat cable, and the CC2640 core processor supplies power and also provides a ground potential to the front-end flexible blood oxygen saturation detection circuit through the FPC connection flexible flat cable.

6. The blood oxygen saturation detection system according to claim 1, wherein a volume of the front-end flexible blood oxygen saturation detection circuit is less than 18 m×18 mm×2 mm, the CC2640 core processor is a single-layer circuit, and an area of the CC2640 core processor is less than 28 mm×28 mm.

7. The blood oxygen saturation detection system according to claim 1, wherein the mobile terminal is a mobile phone or a PC, or other device or system which can receive and display measurement data and carry out calculation of blood oxygen saturation.

* * * * *